(12) United States Patent
Cawley et al.

(10) Patent No.: US 9,274,090 B2
(45) Date of Patent: *Mar. 1, 2016

(54) ULTRASONIC NON-DESTRUCTIVE TESTING

(71) Applicant: Imperial Innovations Limited, London (GB)

(72) Inventors: Peter Cawley, London (GB); Frederick Bert Cegla, Middlesex (GB)

(73) Assignee: Imperial Innovations Limited, London (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/291,467

(22) Filed: May 30, 2014

(65) Prior Publication Data

US 2014/0260633 A1   Sep. 18, 2014

Related U.S. Application Data

(63) Continuation of application No. 13/712,492, filed on Dec. 12, 2012, now Pat. No. 8,789,419, which is a continuation of application No. 12/891,231, filed on Sep. 27, 2010, now abandoned, which is a continuation of application No. 12/092,630, filed as application No. PCT/GB2006/003415 on Sep. 14, 2006, now Pat. No. 8,381,592.

(30) Foreign Application Priority Data

Nov. 4, 2005   (GB) .................................. 0522572.7

(51) Int. Cl.
*G01N 29/28* (2006.01)
*G01N 29/34* (2006.01)
(Continued)

(52) U.S. Cl.
CPC .............. *G01N 29/34* (2013.01); *G01N 29/069* (2013.01); *G01N 29/2412* (2013.01);
(Continued)

(58) Field of Classification Search
CPC ... G01N 29/34; G01N 29/28; G01N 29/2412; G01N 29/069; G01N 2291/0234; G01N 2921/0422; G01N 2291/02854; G01N 2291/0421; G10K 11/24
USPC ........................................... 73/617, 644, 596
See application file for complete search history.

(56) References Cited

U.S. PATENT DOCUMENTS 3,296,561 A   1/1967   Polucci
3,299,695 A   1/1967   Dickinson, III
(Continued)

FOREIGN PATENT DOCUMENTS

CN   1605862   4/2005
GB   2092408   8/1982
(Continued)

OTHER PUBLICATIONS

International Search Report for PCT/GB2006/003415, Completed by the European Patent Office on Jan. 22, 2007, 3 Pages.
(Continued)

*Primary Examiner* — Laura Martin
*Assistant Examiner* — Rose M Miller
(74) *Attorney, Agent, or Firm* — Brooks Kushman P.C.

(57) ABSTRACT

An apparatus and method for ultrasonic non-destructive testing provides an elongate strip of ultrasound transmissive material coupled at a proximal end to an object under test. The elongate strip has a transverse cross-section with a width and thickness giving an aspect ratio greater than unity and matched to the ultrasonic transducer such that excitation induces a substantially non-dispersive ultrasonic signal to propagate along the elongate strip to the proximal end and to enter the object under test. These non-dispersive pulses are particularly suited for time-of-flight measurements, thickness measurements, crack measurements and the like. The elongate strip helps to separate the transducer from a potentially hostile environment associated with the object under test. The elongate strip also has a large area of contact with the object under test allowing efficient transmission of energy into the object under test.

12 Claims, 6 Drawing Sheets

(51) Int. Cl.
    *G01N 29/06*    (2006.01)
    *G01N 29/24*    (2006.01)
    *G10K 11/24*    (2006.01)
(52) U.S. Cl.
    CPC ............... *G01N 29/28* (2013.01); *G10K 11/24* (2013.01); *G01N 2291/0234* (2013.01); *G01N 2291/02854* (2013.01); *G01N 2291/044* (2013.01); *G01N 2291/0421* (2013.01); *G01N 2291/0422* (2013.01)

(56)          References Cited

U.S. PATENT DOCUMENTS

| | | | |
|---|---|---|---|
| 3,581,247 | A | 5/1971 | Belford et al. |
| 3,806,840 | A | 4/1974 | Whitney et al. |
| 4,014,211 | A | 3/1977 | Araki et al. |
| 4,352,038 | A | 9/1982 | Moreton |
| 5,159,838 | A | 11/1992 | Lynnworth |
| 5,828,274 | A | 10/1998 | Jen et al. |
| 5,962,790 | A | 10/1999 | Lynnworth et al. |
| 6,047,602 | A | 4/2000 | Lynnworth |
| 6,230,568 | B1 | 5/2001 | Winston et al. |
| 6,349,599 | B1 | 2/2002 | Lynnworth et al. |
| 6,400,648 | B1 | 6/2002 | Heijnsdijk et al. |
| 8,381,592 | B2 | 2/2013 | Cawley et al. |

FOREIGN PATENT DOCUMENTS

| | | |
|---|---|---|
| GB | 2164220 | 3/1986 |
| JP | 2003269944 | 9/2003 |
| JP | 2004085370 | 3/2004 |

OTHER PUBLICATIONS

Office Action dated Jan. 27, 2014 in corresponding Chinese Appn. No. 20101519914 (published Feb. 16, 2011 as CN 101976562), 7 pgs.

Guan-Cheng, Li et al., "New Technology and developing Trends of the Multi-Boundary Non-Destructive Ultrasonic Detection," Chinese Journal of Nature, 2003, Issue 4, pp. 233-236 (Google Translate English translation attached, 12 pages).

Mindlin et al. "Vibrations and Waves in Elastic Bars of Rectangular Cross Section", The Journal of Applied Mechanics, Mar. 1960, p. 152-158.

Achenbach, Wave Propagation in Elastic Solids, 1975, Section 7.6: Half-Space Subjected to Antiplane Surface Disturbances, North-Holland Publishing Company, pp. 283-289.

Hayashi et al. "Guided Wave Dispersion Curves for a Bar with an Arbitrary Cross-Section, A rod and Rail Example", Ultrasonics 2003, vol. 41, p. 175-183.

Lamb, "On the Propagation of Tremors over the Surface of an Elastic Solid", Philosophical Transactions of the Royal Society of London. Series A, Containing Papers of a Mathematical of Physical Character 1904, vol. 203, p. 1-42.

Lynnworth et al. "Extensional Bundle Waveguide Techniques for Measuring Flow of Hot Fluids", IEEE Transactions on Ultrasonic, Ferroelectrics and Frequency Control, Apr. 2005, vol. 52, No. 4, p. 538-544.

Miller et al. "The Filed and Radiation Impedance of Mechanical Radiators on the Free Surface of a Semi-Infinite Isotropic Solid", Proceedings of the Royal Society of London, Series A, Mathematical and Physical Sciences May 20, 1954, vol. 223, No. 1155, p. 521-541.

Mukdadi et al. "Elastic Guided Waves in a Layered Plate with Rectangular Cross Section", J. Acoust. Soc. Am. Nov. 2002, vol. 115, No. 5, Part 1, p. 1766-1779.

Sather, "Ultrasonic Buffer-Rod Technique for the High-Temperature Measurement of the Elastic Moduli of Short Specimens", The Journal of the Acoustical Society of America Nov. 1967, vol. 43, No. 6, p. 1291-1294.

Wilcox et al. "Dispersion and Excitability of Guided Acoustic Waves in Isotropic Beams with Arbitrary Cross Section", Review of Quantitative Nondestructive Evaluation Ed. by D.O. THompson and D. E. Chimenti, vol. 21, p. 203-210.

Wilcox et al. "The effect of Dispersion on Long-Range Inspection Using Ultrasonic Guided Waves", NDT&E International 2001, vol. 34, p. 1-9.

Wilcox, "A Rapid Signal Processing Technique to Remove the Effect of Dispersion from Guided Wave Signals", IEEE Transactions on Ultrasonics, Ferroelectrics, and Frequency Control Apr. 2003, vol. 50, No. 4, p. 419-427.

Cegla et al. "Material Property Measurement Using the Quasi-Scholte Mode—A Waveguide Sensor", J. Acoust. Soc. Am. Mar. 2005, vol. 117, No. 3, Part 1, p. 1098-1107.

ULTRASONIC NON-DESTRUCTIVE TESTING

CROSS-REFERENCE TO RELATED APPLICATIONS

This application is a continuation of U.S. application Ser. No, 13/712,492 filed Dec. 12, 2012, which is a Continuation of U.S. application Ser. No. 12/891,231 filed Sep. 27, 2010, now pending, which is a Continuation of U.S. application Ser. No. 12/092,630 filed Aug. 26, 2008, now U.S Pat. No. 8,381, 592 issued Feb. 26, 2013, which is a 371 national phase of PCT/GB2006/03415 filed Sep. 14, 2006 which, in turn, claims priority to GB Application No. 0522572.7 filed Nov. 4, 2005, the disclosures of which are incorporated in their entirety by reference herein.

BACKGROUND OF THE INVENTION

1. Field of the Invention

The present invention relates to an apparatus and method for ultrasonic non-destructive testing.

2. Description of the Prior Art

The use of ultrasonic signals in the non-destructive testing of materials is known. Thickness measurements may be carried out by sending ultrasonic signals into a test material and measuring their time-of-flight across the sample. Defect monitoring may be performed by sending ultrasonic signals into a test material and observing their reflection from the structure of a defect. Typically, an ultrasonic transducer is placed in direct contact with the object under test. Transmitted ultrasonic signals are then received by the transmitting transducer also acting as a receiving transducer, or a second receiving transducer may be employed. Such procedures are straightforward in non-hostile environments, but significant technical obstacles must be overcome in order to operate such transducers in hostile (e.g. high temperature) environments.

The development of ultrasonic transducers and their ancillary components capable of withstanding high temperatures for extended periods of time is challenging. Most transducer materials are adversely affected by high temperatures and furthermore, resilient buffer amplifiers are required to convert signals for transmission along coaxial cables, which themselves must withstand the environment. Suitable connectors and power supplies must also be provided.

An attractive alternative would be to use an acoustic waveguide made from a material capable of withstanding the hostile environment to transmit the ultrasonic signal into the test object from a transducer and ancillary components located in a non-hostile region. The end of the waveguide would be attached directly to the region of interest of the test sample. The use of an intermediary waveguide, however, is not a trivial task. Ultrasonic inspection typically employs high frequency (>1 MHz) pulsed waveforms, which are not easily transmitted along a long waveguide with high fidelity, due to dispersion, multiple modes and attenuation. Additionally, both the transducers and the test sample must be efficiently coupled to the waveguide to avoid prohibitively high energy losses.

A major problem to be overcome is dispersion and the presence of multiple modes. FIG. 1 of the accompanying drawings shows dispersion curves for a cylindrical rod waveguide. Some spread in the energy of the transmitted signal is unavoidable, so for example a signal generated at a centre frequency of 2 MHz will typically have energy between 1 MHz and 3 MHz. Hence, since the accurate identification and timing of ultrasonic signals coming from the test sample is paramount to the non-destructive testing procedures described above, it is highly desirable to transmit a signal which is largely non-dispersive, i.e. its velocity is almost constant with frequency, and is dominated by a single mode.

Dispersion in a waveguide and the possible modes are largely a function of the product of the frequency of the signal and the smallest dimension of the waveguide. Furthermore, in order to obtain good accuracy for ultrasonic thickness gauging it is generally necessary to operate at above 1 MHz. However, at higher frequency-dimension products more higher order modes may propagate and thus it is necessary to limit the smallest dimension of the waveguide. Accordingly, the use of thin rod waveguides is known in the art. Such devices are not without their own difficulties though, since it is difficult to transfer sufficient energy into the thin rod to produce a strong signal. Also, when a thin waveguide is joined to a larger structure there is a strong surface reflection and relatively little energy enters the structure. Additionally, a thin rod waveguide coupled to the surface of a structure effectively acts as a point source, from which energy spreads spherically, meaning that little energy returns to the receiving waveguide, even from a strong reflector, such as the bottom surface of the structure.

U.S. Pat. No. 5,962,790 (for example—see Refs 1, 2 and 3 and also Ref 4) discloses a system using thin wire to minimize dispersion and overcoming some of the problems of a single thin wire by employing a bundle of thin wires. Each wire operates at a suitably low frequency-diameter product, yet significantly more energy may be transmitted through the multiple parallel wires in the bundle than through a single wire. Nevertheless, bundles of wires are relatively expensive to produce and become rather inflexible as their diameter increases, limiting the geometries in which they may be deployed. Furthermore, cross-talk between individual wires may complicate the signal analysis and there are practical difficulties associated with either attaching each individual wire to the test structure, or terminating the bundle with a plate which does not introduce dispersion problems. In terms of mode excitation, either extensional modes or a torsional mode may be excited in a single wire. A torsional mode is usually excited by a transducer in contact with the side of the wire, or by an encircling electromagnetic coil. Such techniques are not practical for a bundle of wires, where realistically only extensional modes may be used.

U.S. Pat. No. 6,400,648 (Ref 5) discloses a coiled foil waveguide as an alternative to a bundle of rods. The thickness of the foil is arranged to be much smaller than the smallest wavelength of the propagated signal, satisfying the low frequency-dimension product for non-dispersive transmission. The foil is coiled around an axis_parallel to the direction of signal propagation, so if unwrapped would be very long in a direction perpendicular to the direction of signal propagation. However as the diameter of the coil increases, the waveguide becomes rigid and damping due to rubbing between the layers may occur. Like a bundle of wires, a coiled foil is better suited to extensional rather than torsional waves.

U.S. Pat. No. 5,828,274 (Ref 6) discloses a tapered ultrasonic waveguide with an external layer of attenuative cladding. The cladding removes the effects of the waveguide boundaries by damping and limiting surface reflections. This has the effect of removing almost all trailing echoes, however the effects of dispersion are not entirely removed and the signal is slightly delayed, slightly distorted and strongly attenuated. The latter disadvantage limits the length of such a waveguide, which is also rather inflexible. This is an improvement over previous proposals using non-uniform threaded bars as waveguides (see Refs 7 and 8).

U.S. Pat. No. 6,047,602 discloses an ultrasonic waveguide for fluid flow metering which is a rectangular cross sectioned bar with an angled end section. A surface of the angled section reflects energy travelling along the bar into a narrow directed beam to enter the test fluid. The waveguide is designed to maximize the energy transfer across a conduit. This device has significant disadvantages in the field of thickness measurement or defect monitoring, being inflexible and the wave propagation not being optimized for a clean undistorted signal shape, which is of utmost importance for timing measurements in the non-destructive inspection of a sample.

This is a technical problem of providing a practical apparatus for ultrasonic non-destructive testing capable of operating in hostile environments and addressing the above described problems.

SUMMARY OF THE INVENTION

According to the present invention there is provided an apparatus for ultrasonic non-destructive testing of an object under test, said apparatus comprising:

an elongate strip of ultrasound transmissive material, said elongate strip having a proximal end for coupling to said object under test and a distal end; and an ultrasonic transducer coupled to said elongate strip; wherein said elongate strip has a transverse cross-section with a width and a thickness giving an aspect ratio greater than unity and matched with said ultrasonic transducer such that excitation of said ultrasonic transducer induces substantially non-dispersive ultrasonic signals to propagate along said elongate strip to said proximal end and to enter said object under test.

The present invention recognizes that there is a need for ultrasound signals for non-destructive purposes to be transmitted in a substantially non-dispersive manner, such that precise timing measurements may be made. The present invention further recognizes that there is a need for an ultrasound transmission component to be flexible, such that the apparatus may be deployed in awkward geometries. Accordingly, by transmitting ultrasonic signals along an elongate strip with a width and thickness aspect ratio greater than unity and by exciting signals which are substantially non-dispersive, ultrasonic non-destructive testing of a test object may be performed in environments hostile to traditional ultrasound transducers and in configurations which require the transmission component to flexibly circumvent intervening objects.

The elongate strip is formed of a material having a shear velocity $C_S$ and a shear wavelength $\lambda_B$, where $\lambda_B = C_s/F$ and F is the frequency corresponding to $\lambda_B$, and said substantially non-dispersive ultrasonic signals are formed of components of different frequencies and having shear wavelengths extending from $\lambda_{Short}$ to $\lambda_{Long}$. Some shear modes of ultrasonic waves are advantageously non-dispersive and have the shortest wavelengths. Shorter wavelengths provide finer spatial resolution for inspection purposes.

In a similar manner said elongate strip is formed of a material having a bar velocity $C_{bar}$ and a bar wavelength $\lambda_{bar}$, where $\lambda_{bar} = C_{bar}/F$ and F is the frequency corresponding to $\lambda$bar, and said substantially non-dispersive ultrasonic signals are formed of components of different frequencies and having bar wavelengths extending from $\lambda_{short}$ to $\lambda_{long}$. Compressional waves may be better suited to some situations.

Whilst the dimensions of the elongate strip can vary considerably, in preferred embodiments, the thickness of the elongate strip will be less than 2.5 times $\lambda_{short}$. In particularly preferred embodiments the thickness of the elongate strip will be less than $\lambda_{short}$. Such dimensional limitations help avoid the excitation of undesirable higher order modes.

In preferred embodiments said width is greater than 3.5 $\lambda_{long}$. In still more highly preferred embodiments said width is greater than 5 $\lambda_{long}$. Such dimensional limitations help provide that the ultrasonic wave propagation is substantially non-dispersive, has low amplitude at the waveguide edges and that the mode shape is approximately constant.

Whilst differing ultrasonic modes may be used in preferred embodiments, said substantially non-dispersive ultrasonic signals comprise lowest order shear mode vibrations with a polarisation perpendicular to the propagation direction and parallel to said width. Such signals may be transmitted with low distortion and high efficiency along a waveguide as described above.

In other embodiments, said substantially non-dispersive ultrasonic signals comprise lowest order compression mode vibrations with polarisation parallel to the propagation direction. The use of such waves is beneficial in applications where high shear wave attenuation is encountered in the test object or where the use of compressional waves in the test object is advantageous.

Whilst the simultaneous excitation of multiple modes of a suitable type is possible, in preferred embodiments, said ultrasonic transducer excites substantially only a single mode of propagated guided wave. In other embodiments said ultrasonic transducer is apodised to excite substantially only said single mode of propagating guided wave to induce said substantially non-dispersive ultrasonic signals. The restriction to a single mode is advantageous in applications which require precise timing information, since separately received signals can more readily be identified as coming from separate features in the test object rather than being the result of different modes.

Relative to the desired propagation distances in the object under test, in preferred embodiments, said substantially non-dispersive ultrasonic signals spread substantially cylindrically from said proximal end to said object under test. The decay rate of the amplitude of a cylindrically spreading wave is proportional to the reciprocal of the square root of the distance from the source, whereas the amplitude of a spherically spreading wave is proportional to the reciprocal of the distance from the source. The former propagation therefore loses less energy.

Whilst the transducer could be attached to a variety of positions on the elongate strip, in preferred embodiments, said ultrasonic transducer may advantageously be coupled to said distal end. In this context said ultrasonic transducer is coupled to said distal end by one of:
(i) a bonded connection;
(ii) a mechanical fixing and ultrasound transmissive couplant; and
(iii) a mechanical fixing and variable force.

Such couplings between the ultrasonic transducer and the distal end of the waveguide promote efficient energy transfer between the two. Bonding includes welding and brazing as well as other bonding techniques.

The coupling of the transducer to the elongate strip can be achieved in a number of different ways. In one preferred embodiment said ultrasonic transducer comprises a transducer coupled to at least one longitudinal side of said elongate strip. In another preferred embodiment said ultrasonic transducer comprises a coil operable to provide electromagnetic ultrasound transduction. Such arrangements allow alternative efficient methods of exciting ultrasonic signals in the waveguide.

In one embodiment of the present invention said elongate strip is bent around an axis that is substantially parallel to said width of said elongate strip and substantially perpendicular to the propagation direction. This allows particularly easy routing of the ultrasonic signals in confined real life situations.

The receipt of the ultrasonic signal can be provided in a variety of different manners. In one preferred embodiment, said apparatus comprises an ultrasound receiver operable to receive reflected ultrasound from said object under test resulting from said substantially non-dispersive ultrasonic signals entering said object under test. In this context, said ultrasound receiver comprises one or more further elongate strips each coupled to said object under test at a respective position to receive said reflected ultrasound and having a receiving ultrasonic transducer to detect said reflected ultrasound. In another preferred embodiment, said elongate strip and said ultrasonic transducer also form said ultrasound receiver.

Whilst a variety of ultrasonic testing methodologies may be used in conjunction with the present technique, in a preferred embodiment, said reflected ultrasound comprises at least one reflected signals and said ultrasound receiver measures a time difference between said reflected signals. Such a time difference measurement gives information about the structure of the test object.

The present invention recognizes that whilst the coupling of said elongate strip to said object under test can be achieved in many different ways, it is important to the performance of said apparatus and in a preferred embodiment, said proximal end is fixed to said object under test by one of:
(i) welding;
(ii) brazing;
(iii) soldering; and
(iv) bonding.

In another preferred embodiment, said proximal end is clamped to said object under test. In this context, the coupling may be improved by ultrasound transmissive couplant being disposed between said proximal end and said object under test. Furthermore, improved coupling may be achieved in an embodiment wherein a clamp clamps said elongate strip to said object under test with an adjustable force. In preferred embodiments said clamp is coupled to said object under test by studs welded to said object under test. Another preferred form of clamp is one that is wrapped around the object under test, e.g. around a pipe.

The present technique is particularly useful when said ultrasonic non-destructive testing is thickness measurement or crack monitoring.

The present techniques are particularly well suited to situations in which said object under test is:
(i) at a temperature greater than 200° C.; and
(ii) subject to above background levels of ionising radiation.
Viewed from a second aspect the present invention provides a method of ultrasonic non-destructive testing of an object under test, said method comprising:
coupling a proximal end of an elongate strip to an object under test;
exciting substantially non-dispersive ultrasonic signals within said elongate strip to propagate along said elongate strip and to enter said object under test.

Embodiments of the invention will now be described, by way of example only, with reference to the accompanying drawings in which:

DETAILED DESCRIPTION OF THE PREFERRED EMBODIMENT(S)

Figure 1:
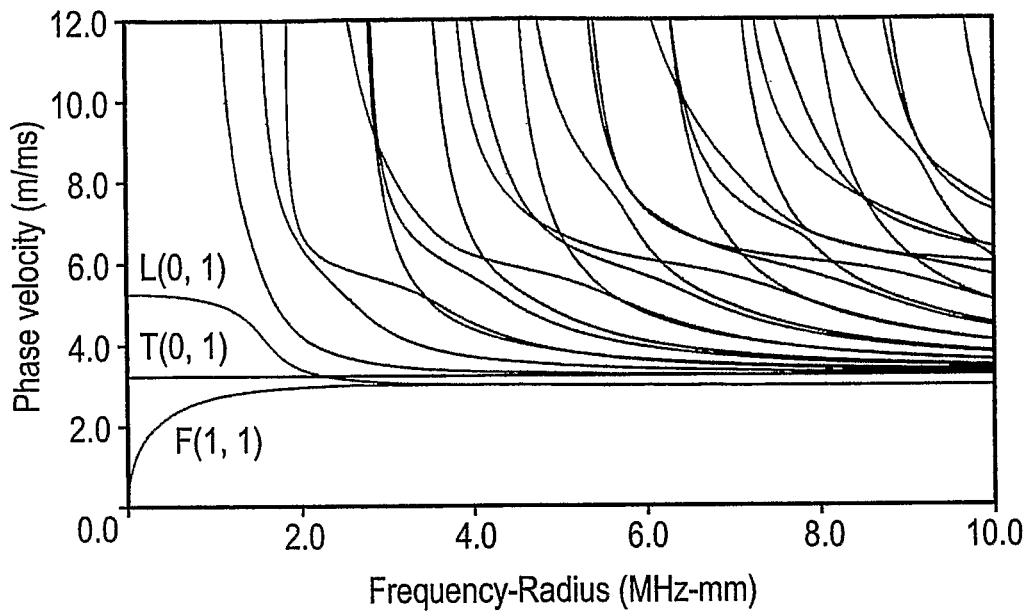
FIG. 1 illustrates the phase velocity dispersion curves for various ultrasonic modes in a steel rod.
Figure 2:
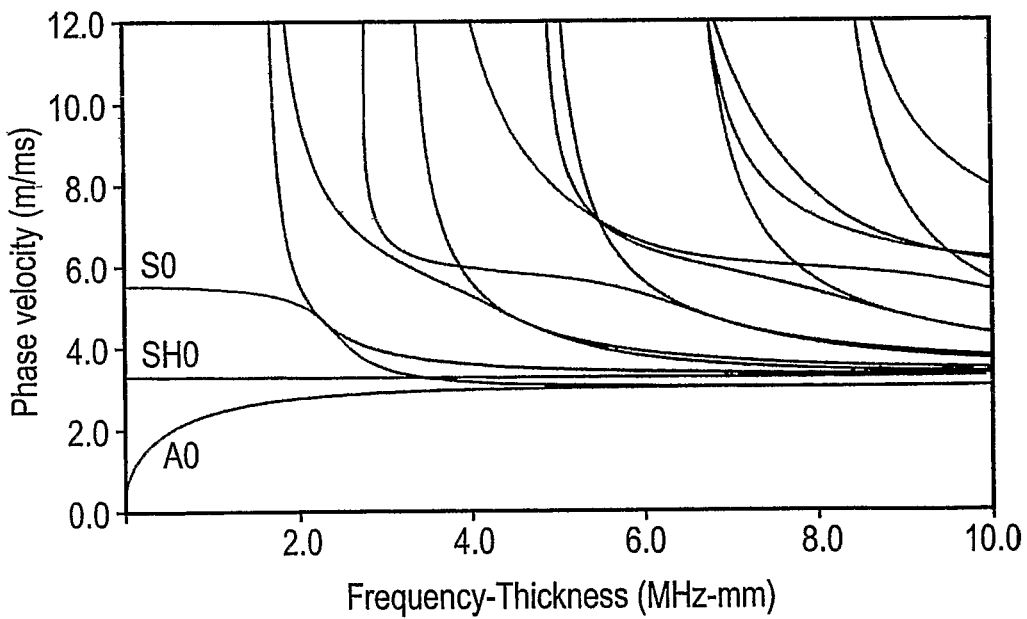
FIG. 2 illustrates phase velocity dispersion curves for various ultrasonic modes for a steel plate.

The present technique uses a thin strip waveguide (an elongate strip). The phase velocity dispersion curves for a plate are shown in FIG. 2 as a function of the frequency-thickness product. Below 1.4 MHz-mm only three modes can propagate: S0 (the lowest order compression wave with polarisation parallel to propagation), A0 (the flexural wave at low frequencies) and SH0 (the lowest order shear mode with polarisation perpendicular to propagation and parallel to strip width). These waves are analogous to the L(0,1), F(1,1) and T(0,1) modes in the rod respectively. The A0 mode is highly dispersive and is not attractive for testing purposes but the S0 mode is minimally dispersive at low frequencies while the SH0 mode is completely non-dispersive at all frequencies. FIG. 2 shows that in the frequency range below 1.4 MHz-mm the phase velocity of the SH0 mode is much lower than that of the S0 mode. Since the wavelength is given by the phase velocity divided by the frequency it follows that at a given frequency the SH0 mode has a shorter wavelength than the S0 mode. This often makes it more sensitive in inspection applications. Preferred embodiments of the present technique therefore use shear horizontal modes but there may be circumstances where compressional modes like the S0 mode are preferable (for example in applications where the shear wave attenuation is much higher than that of the extensional wave so that the signals with the shear wave are too weak to be used).

Use of the strip waveguide has the following advantages over the single wire, bundle and coiled solutions proposed previously:
Since the cross sectional area is much higher than a single wire, it is easier to obtain strong signals; also the reflection from the interface between the waveguide and the structure is smaller so more energy enters the test structure.

When the wave enters the test structure from the strip it tends to spread cylindrically. This means that the wave amplitude in the structure decreases at a rate proportional to 1/r due to beam spreading where r is the distance from the attachment point. This compares with a decay rate proportional to 1/r for a wire system where the beam spreading is spherical.

Figure 3:
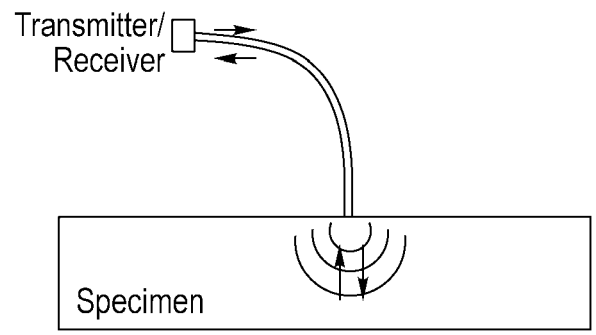
FIG. 3 schematically illustrates thickness gauging using a waveguide sensor.
Figure 4:
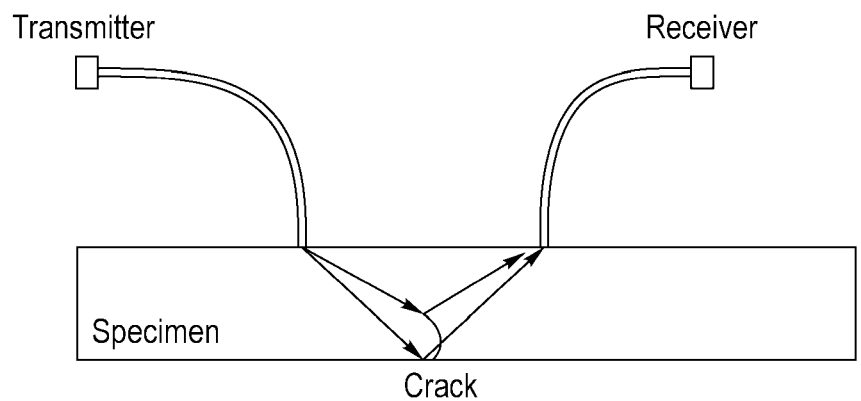
FIG. 4 schematically illustrates time of flight diffraction using a waveguide sensor.

The cylindrical beam spread pattern is very suitable for both simple thickness gauging and crack sizing based on time of flight diffraction (TOFD) (See FIG. 3 and FIG. 4).

It is easy to excite a shear wave or a longitudinal wave in the strip by attaching a transducer to the end of the strip; it is also possible to excite either type of wave by attaching appropriate transducers to the sides of the strip if this is more convenient.

It is possible to weld, solder, braze or bond the wave guide to the structure. It is also possible simply to use viscous ultrasonic gel couplant at low temperatures and/or to tightly clamp the waveguide onto the structure (e.g. by welded on threaded studs giving an adjustable clamping force) which works at high and low temperatures. Since the waveguide is thin it is relatively easy to ensure that the whole bottom surface of the waveguide is attached to the structure, so improving signal transmission. Clamping the waveguide to the structure can be advantageous since it removes the drawback of undesirable geometric distortions that are inevitably introduced by permanent joining techniques. Adequate signal transmission can be achieved by clamping.

The strip waveguide is much more flexible in one direction than a typical bundle so it is easier to access structures around corners.

Figure 5:
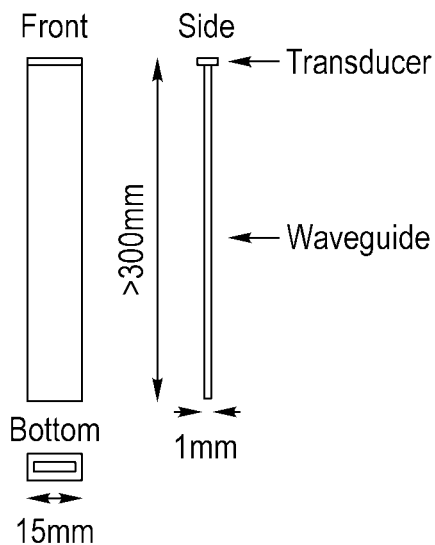
FIG. 5 schematically illustrates some example dimensions of an elongate strip forming part of a sensor in accordance with the present techniques.
Figure 6:
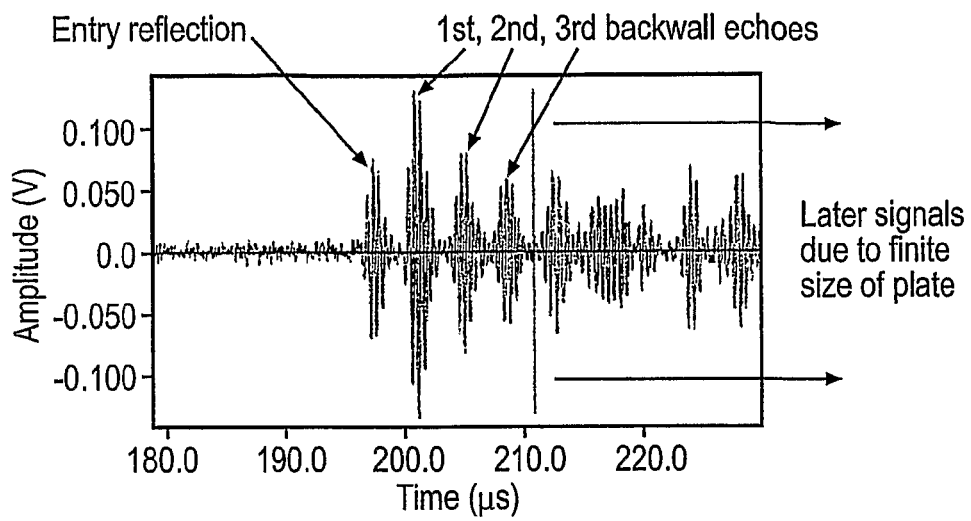
FIG. 6 illustrates an example time trace received using a 1 by 15 mm strip of lengths 300 mm from a plate (50 by 50 mm) of 6 mm thickness using a signal with a 2 MHz centre frequency.

FIG. 5 shows an example embodiment of the invention. FIG. 6 shows signals received in the thickness gauging application of FIG. 3 where the thickness can be obtained from the time between the top surface and bottom surface reflections or between successive backwall echoes knowing the speed of sound. The sample may be at high temperature, e.g. >200° C., and/or subject to above background levels of ionising radiation.

The thickness of the strip should generally be chosen so that the product of the thickness and the maximum frequency excited is less than 3 MHz-mm for SH type waves and 1.4 MHz-mm for longitudinal type waves in order to avoid the excitation of higher order modes across the thickness. If a longitudinal wave is used it is also often desirable to use a lower frequency-thickness product in order to minimize dispersion, though it is also possible to compensate for dispersion (see Ref 10). The width of the strip is also an important parameter.

When the elongate strip is formed of a material having a shear velocity $C_s$, and a shear wavelength $\lambda_B$, where $\lambda_B = C_s/F$ and F is the frequency corresponding to $\lambda_B$, and said substantially non-dispersive ultrasonic signals are formed of components of different frequencies and having shear wavelengths extending from $\lambda_{short}$ to $\lambda_{Long}$. It is desirable, but not essential, that the thickness be less than 2.5 $\lambda_{short}$ and particularly preferred to be less than $\lambda_{short}$. Similarly, it is preferred that the width is greater than 3.5 $\lambda_{Long}$ and particularly preferred that it is greater than 5 $\lambda_{Long}$. In a similar way the same preferred ranges apply when said elongate strip is formed of a material having a bar velocity Cbar and a bar wavelength $\lambda_{bar}$, where $\lambda_{bar} = C_{bar}/F$ and F is the frequency corresponding to $\lambda_{bar}$, and said substantially non-dispersive ultrasonic signals are formed of components of different frequencies and having bar wavelengths extending from $\lambda_{short}$ to $\lambda_{long}$.

The dispersion curves in FIG. 2 model the wave propagation in a plate of infinite width. Structures with a very large width to thickness ratio will be modelled extremely accurately by this infinite width assumption. However the closer the side surfaces are moved together to create a strip of rectangular cross-section the more the wave propagation will be influenced by the presence of the boundaries of the strip. Mindlin and Fox (see Ref 11) were the first to describe the propagating modes of a bar of rectangular cross section. Their solution was made up of a superposition of several flexural, longitudinal and shear modes that propagate in an infinite plate of the width and thickness of the bar respectively. The solutions for the infinite plate were superposed in order to fulfill the boundary conditions of zero stress all around the perimeter of the cross section. This method enabled them to determine the dispersion characteristics of the bar at distinct frequencies and aspect ratios of the bar. A solution for all frequencies and aspect ratios was however not possible. More recently however the continuous tracing of dispersion curves for wave propagation in structures of arbitrary cross section has become possible through the use of finite element (FE) eigensolvers. Wilcox et al. (see Ref 12), Mukdadi et al. (see Ref 13) and Hayashi et al. (see Ref 14) have reported methods of tracing dispersion curves for L-shaped sections, rail heads and strips.

Figure 7:
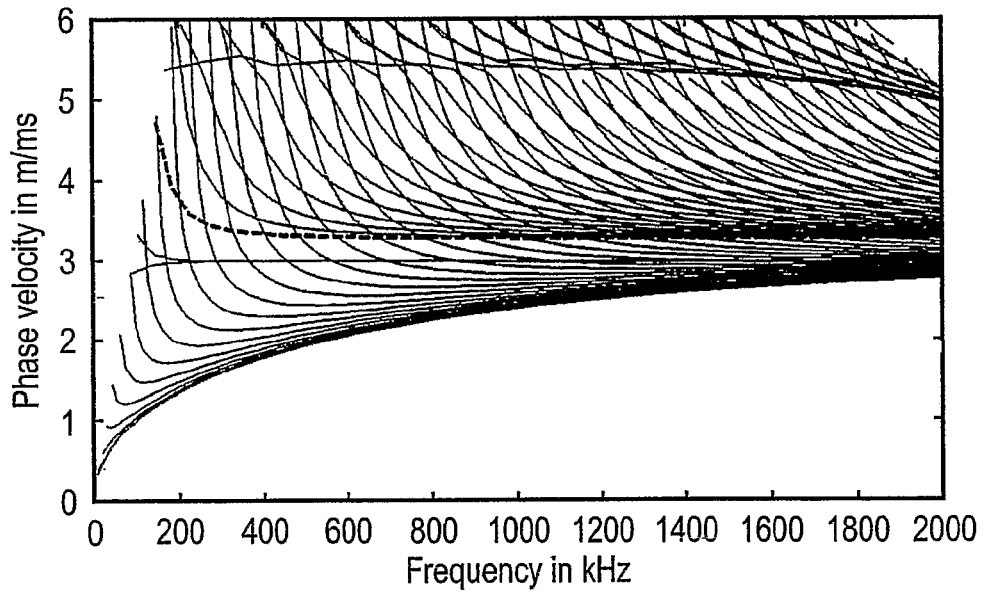
FIG. 7 shows phase velocity dispersion curves for ultrasonic modes within a 1 by 30 mm elongate steel strip, highlighting the lowest order shear horizontal mode SH*.

The method of Wilcox et al. has been employed here to analyse the modes propagating in a 1 mm thick and 30 mm wide strip of steel. FIG. 7 shows the phase velocity dispersion curves. The mode highlighted by the thicker line has been identified as the first shear horizontal mode SH* of this strip. In contrast to the infinite plate case the propagating SH0 mode does not exist in a finite strip. This is due to the zero stress boundary condition on the strip sides, which can only be satisfied by rigid body motion or the SH* and higher order modes. As a consequence no non-dispersive propagating shear mode exists in a strip of finite width. However the thicker the strip, the lower the cut-off frequency of the SH* mode becomes. Since the SH* mode asymptotes to the bulk shear velocity in the material it becomes virtually non-dispersive at higher frequencies. In this invention the use of pure virtually non-dispersive strip modes of compressional or shear nature is used to convey ultrasonic energy along a wave guide or 'acoustic cable' to a specimen that is to be interrogated. The purity of mode avoids the arrival of several signals that could be mistaken for a defect or feature in the interrogated structure and the non-dispersiveness of the mode helps to concentrate wave energy in a narrow time window, which increases the propagation range of the signal in the waveguide and also determines the spatial resolution with which the structure can be monitored (see Ref 15). An example based on the SH* mode will be elaborated here while the use of similar modes of compressional nature is also possible.

Figure 8:
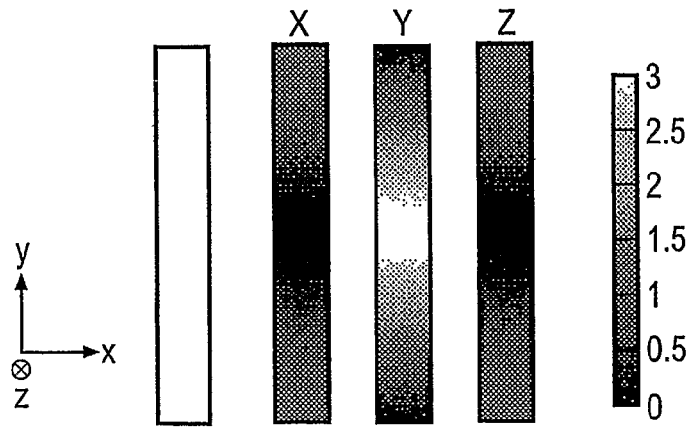
FIG. 8 schematically illustrates a strip cross-section (1 by 15 mm) and SH*(X, Y, Z) displacement mode shape at 2 MHz.
Figure 9:
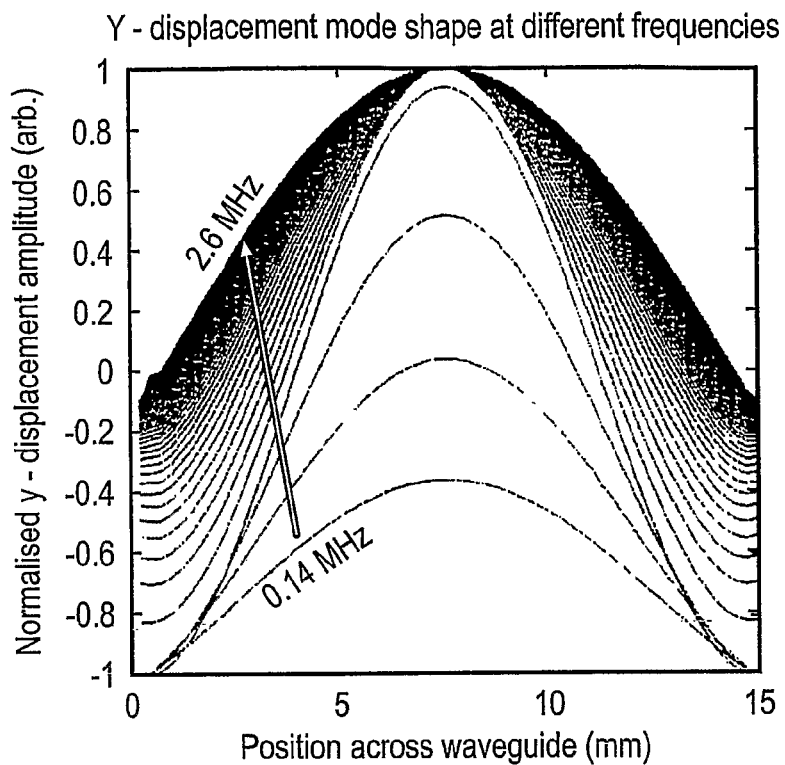
FIG. 9 schematically illustrates SH* Y-displacement mode shape evolution with frequency.

FIG. 8 shows the cross section of a 15 mm wide strip and the mode shape of the SH* mode at 2 MHz. It can be seen that the y displacements, which are displacements parallel to the width direction of the strip, dominate the mode shape of the SH* mode. However unlike the mode shapes of SH modes in infinite plates the mode shapes of SH modes in a strip of finite width change with frequency. FIG. 9 shows the evolution of the dominant y displacement component of the SH* mode over a range of frequencies. The higher the frequency the more the mode concentrates at the centre of the strip. Thus at high frequencies the mode propagates energy at almost the bulk shear velocity along the centre of the strip with little energy and thus sensitivity at the edges.

By means of an apodized transducer, that mimics the mode shape of the mode, pure mode shape excitation can be achieved. Coil transducers may also be used. The transducers can be placed on the ends or the sides of the strip. Since short temporal pulses are broadband signals the mode shape of the mode should not change significantly over the frequency bandwidth of the excitation pulse. At higher frequencies (around centre frequency of 2 MHz) this is the case for the SH* mode of strips of larger width. Therefore there are two criteria that govern the allowable range of aspect ratios of the strip. The first is that the mode is virtually non-dispersive (velocity variations of less than 5%) in the frequency bandwidth of interest and the second is that a relatively constant mode shape over the frequency bandwidth of interest exists (less than 10% difference in normalized amplitudes). For the SH* mode it is now the task to find the limit of aspect ratio for which both criteria are satisfied.

Figure 10:
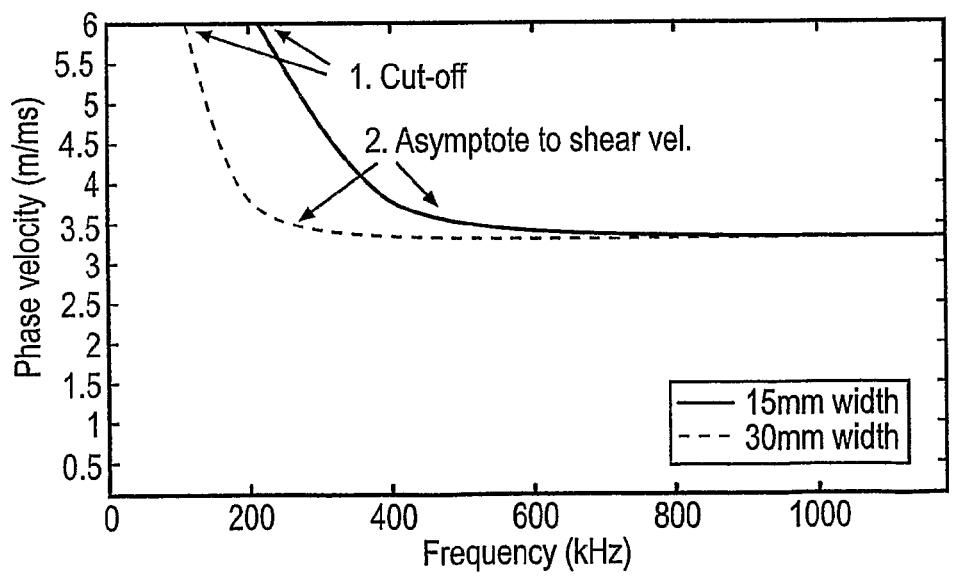
FIG. 10 schematically illustrates the phase velocity for the lowest order shear type mode SH* whose dispersion curve is highlighted in FIG. 7 when propagating in strips of cross-section 1 by 30 mm and 1 by 15 mm respectively.
Figure 11:
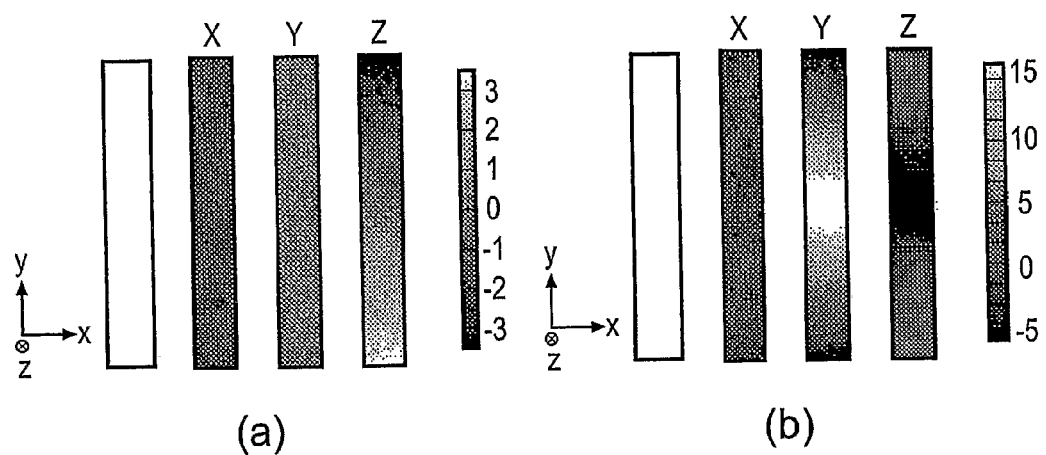
FIG. 11 schematically illustrates SH*(X, Y, Z) displacement mode shape (1 by 15 mm cross-section) near cut off 0.14 MHz and at 0.5 MHz near the bend to asymptote.

The dispersion curves for an infinite plate can be made geometry independent by plotting the curves against the frequency thickness (FT) product. Therefore the cut-off mode on a plate twice the thickness of another plate will occur at half the frequency. Since the width/thickness ratio is large (>5) in our case the system can approximately be scaled by two products; the FT product for frequency-thickness of the strip and the FW product for frequency-width of the strip. Reasoning along those lines and keeping the thickness of the strip constant (FT constant), the width of the strip can be adjusted up to a limiting case where the dispersion curves and mode shapes do not fulfill the earlier stated criteria for successful excitation and propagation of a single mode. FIG. 10 shows the SH* mode phase velocity dispersion curves for a 1 mm thick and 30 mm wide strip and a 1 mm thick and 15 mm-wide strip. The cut-off frequency of the mode in the 15 mm wide strip occurs at double the frequency. FIG. 11 shows the mode shape of the SH* mode near the cut-off frequency (point 1.) and at frequencies near the point where the phase velocities start asymptoting (point 2.) towards the shear bulk velocity of the strip. At cut-off the mode exhibits large displacements at the edges of the strip. The displacements at the edges become negligible at higher frequencies.

Useful frequencies for inspection range from 1 MHz-5 MHz. However broadband excitation with pulses is commonly employed in defect and thickness monitoring. This requires a bandwidth of half the centre frequency below and half above the centre frequency of the signal. Thus for a 1 MHz centre frequency pulse the waveguide must exhibit similar non-dispersive wave propagation over the range of 0.5.-1.5 MHz. Similarly for a 2 MHz centre frequency signal this range extends from 1 MHz-3 MHz. As can be seen in FIG. 10, the 1 mm thick and 15 mm wide strip becomes unsuitable for sending a 1 MHz pulse. The phase velocity of the SH* mode has not yet asymptoted to the shear bulk velocity. The mode is still relatively dispersive in the frequency range 500-800 kHz and its mode shape (FIG. 11(*b*)) does not have negligible amplitudes (.about.25%) at the edges. It can also be seen in FIGS. 11(*a*) and (*b*) that until the mode starts to asymptote to the shear wave velocity its mode shape is not dominated by the component in the Y direction. However the same strip is suitable for sending a signal at 2 MHz centre frequency. Within the bandwidth of a 2 MHz signal (1-3 MHz) dispersion is very limited and the mode shape approximately constant (.+−.5%). Therefore for successful wave propagation (in form of the SH* mode) along the strip the frequency-width must be greater than 15 MHz mm. Expressed in a ratio of width over waveguide material bulk shear wavelength the width must be wider than 5 bulk shear wavelengths at the lowest frequency component contained within the signal.

Compressional Waves

The same procedure as above can be carried out for compressional type strip modes. Their use might be beneficial in cases where high shear wave attenuation is encountered in the structure or when the use of compressional waves in the structure is of advantage.

Attachment

The transmission of energy across the 'joint' of the 'acoustic cable' (waveguide) to the structure that is to be monitored is also important. The problem of normal point & line forces on an elastic half space is well known as Lamb's problem and was first solved by Lamb (see Ref 16). Other workers have presented solutions for similar problems with different geometries and source polarizations. Miller and Pursey (see Ref 17) considered infinitely long strips and discs loading the surface normally, tangentially and in torsion. Achenbach (see Ref 18) presented a solution for an infinite line source of anti-plane shear on an elastic half space, which is a simplified 2D solution of a SH* mode in a waveguide entering a larger structure. In this case the anti-plane shear wave excited in the half space radiates cylindrically from the source into the structure. The excitation of a surface wave that occurs under all other loading conditions does not occur in anti-plane shear loading. This is desirable for defect monitoring or thickness gauging since it produces less complicated signals by eliminating mode conversions. Also the radiation patterns described by Miller and Pursey for other sources are more complicated and always contain a surface wave that claims a large fraction of the energy. A strip source for a compressional waveguide is also beneficial compared to a point source since it reduces spherical spreading to cylindrical spreading of the wave from the source. Also the thicker the strip the less energy is converted into a surface wave.

Figure 12:
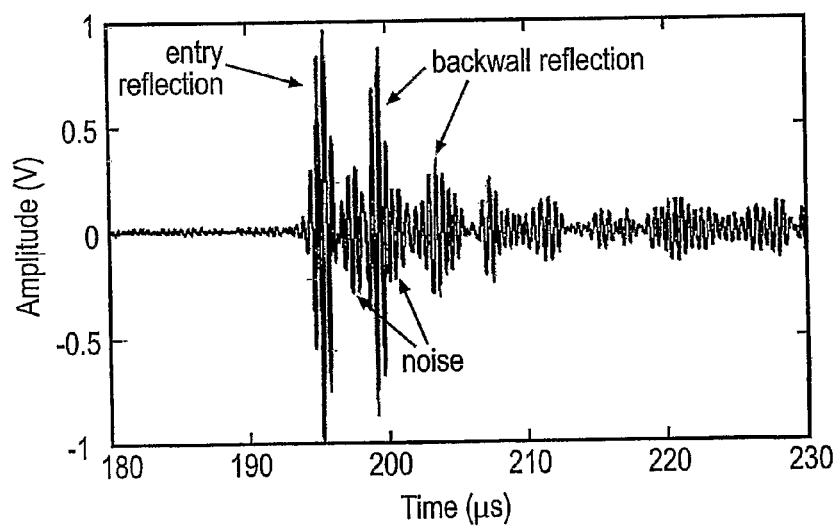
FIG. 12 illustrates a signal from a waveguide welded to a steel plate (6 mm thick)

The method of joining the waveguide to the structure is important. Methods like welding, brazing or soldering as well as clamping dry contact under a large normal force are possible. An attachment by welding or soldering often alters the geometry of entry of the waveguide into the structure. It is probable that fillets, residues of filler metal and flash are produced along the edge where the waveguide meets the structure. It is difficult to remove the fillets or residues, since they are very close to the structure and the waveguide. The large difference in thickness between the thin waveguide and the structure also makes it very difficult to weld or solder the strip onto the structure without damaging it. Changes in geometry introduced by the joining techniques are almost always of the magnitude of the thickness of the waveguide and of the order of a wavelength (at the given frequencies) of a wave in the material. They cause reverberations of the signal within the joint and degrade the signal that returns to the transducer. FIG. 12 shows such a signal of a waveguide welded to a 6 mm back-plate. An entry reflection and a back-wall echo are identifiable; however the signal is covered by a large amount of noise that is due to reverberations in the joint. This can mask weaker signals of features of the structure. Initially it was thought that welding, brazing, soldering or bonding the waveguide to the structure was the best solution to attach the waveguide. Undoubtedly it is the solution that transmits a lot of energy into the structure and is a good option in the pulse-echo mode (send receive on the same transducer). Drawbacks with the permanent joining methods are the contamination of the signal with large noise due to reverberation in the joint. These drawbacks are difficult to remove, therefore in cases where signal "clarity" is important a clamp on method is preferred. The clamped method works in pitch catch mode (send on one transducer receive on another). The signal is injected into the structure via one waveguide and it is picked up by a waveguide that is place right next to the sending waveguide. The signal in the sending strip in 'pulse echo' mode is hardly changed for a clamped or free waveguide. This is because the waveguide and substructure are not in very good contact when they are clamped and pressed together. The large entry reflection, ringing and the presence of other modes (30 dB lower than the signal) completely mask the low amplitude signal from the structure. This problem is overcome by working in pitch catch mode and using another waveguide as pickup for the signal that has been transmitted into the structure. The result is seen in FIG. 6. The pitch catch configuration has the advantage of only picking up the energy that has been transmitted into the structure and therefore reducing the dependence on the ratio of transmitted to reflected amplitude at the joint of waveguide and structure.

Figure 13:
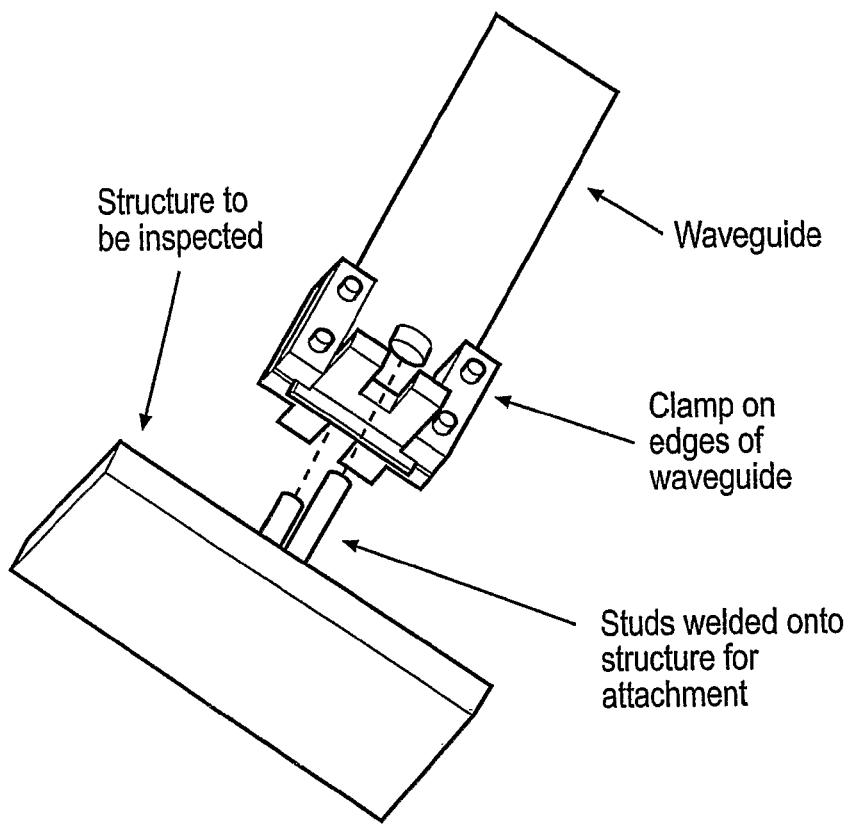
FIGS. 13 and 14 schematically illustrates clamping configurations for attaching a waveguide to a sample under test.
Figure 14:
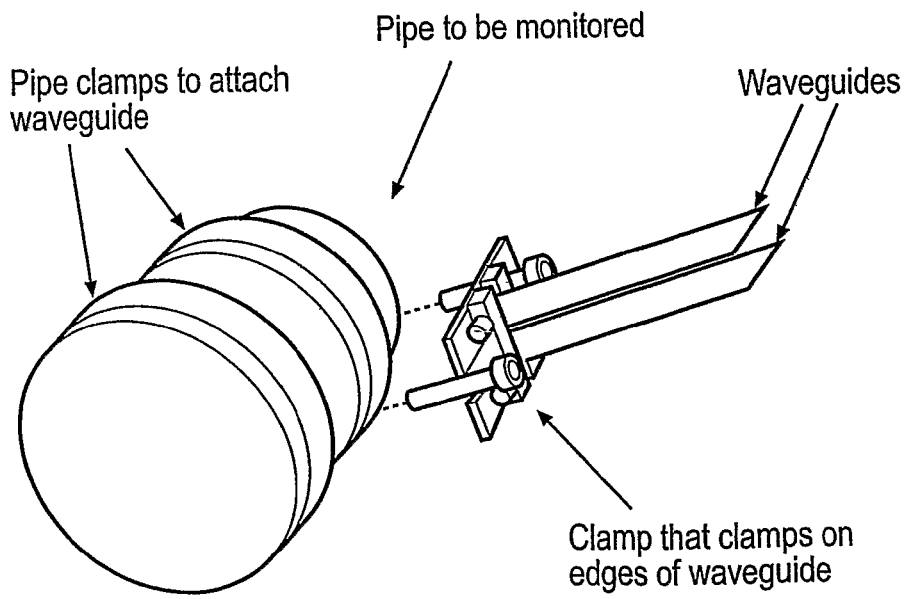

FIG. 13 and FIG. 14 show sketches of possible clamping configurations to a plate like structure and a pipe. In the case of a plate like structure a feature will have to be attached onto the structure that enables the clamped waveguide to be forced onto the surface of the structure. If possible studs can be welded onto the base plate and the waveguide clamp can be screwed onto these studs. There are many more variations possible. FIG. 14 shows a completely detachable solution where the clamped waveguide is attached to the pipe by means of two pipe clamps. It is important to have a clamp that only touches the edges of the waveguide so that it does not influence wave propagation at the centre of the strip. Also a grip close to the end of the waveguide avoids buckling of the thin waveguide when it is forced onto the surface.

REFERENCES

1. Lynnworth, L. C. 'Marginally dispersive ultrasonic waveguides' U.S. Pat. No. 5,159,838, 1992
2. Lynnworth, L. C. 'Ultrasonic path bundle and systems' U.S. Pat. No. 5,962,790, 1999
3. Lynnworth, L. C., Yi Liu, Umina, J. A. 'Extensional bundle waveguide techniques for measuring flow of hot fluids', IEEE Trans UFFC, 52, pp 538-544, 2005.
4. Winston, T. R. and Brunk, J. A. 'Method and apparatus for ultrasonic inspection of inaccessible areas', U.S. Pat. No. 6,230,568, 2001.
5. Heijnsdijk, A. M. and van Klooster, J. M. 'Ultrasonic waveguide', U.S. Pat. No. 6,400,648, 2002.
6. Jen, C. K. and Legoux, J. G. 'Clad Ultrasonic Waveguides with reduced trailing echoes', U.S. Pat. No. 5,828,274, 1998
7. Araki, H. and Matsunaga, Y. 'Ultrasonic Flow Meter', U.S. Pat. No. 4,014,211, 1977
8. Sather, A. 'Ultasonic buffer-rod technique for the high temperature measurement of the elastic moduli of short specimens, J Acous Soc Am 43(6), pp. 1291-1294, 1968
9. Lynnworth, L. C. 'Ultrasonic Buffer/Waveguide', U.S. Pat. No. 6,047,602, 2000
10. Wilcox, P. D., 'A Signal Processing Technique to Remove the Effect of Dispersion from Guided Wave Signals', IEEE Trans. on Ultrason. Ferroelec. and Freq. Cont. 50(4), pp. 419-427, 2003.
11. Mindlin, R. D. and Fox, E. A. 'Vibrations and Waves in Elastic Bars of Rectangular Cross Section', J App Mech, pp. 152-158, 1960
12. Wilcox P., Evans M., Diligent O., Lowe M., Cawley P. 'Dispersion and excitability of guided acoustic waves in isotropic beams with arbitrary cross section', Review of Progress in quantitative NDE 21, D. O. Thompson and D. E. Chimenti, AIP
13. Mukdadi O. M., Desai Y. M., Datta S., Shah A. H., Niklasson A. J. 'Elastic guided waves in a layered plate with rectangular cross section', J Acoust Soc Am 112, pp. 1766-1779, 2002
14. Hayashi T., Song W., Rose J. L. 'Guided wave dispersion curves for a bar with an arbitrary cross-section, a rod and rail example', Ultrasonics 41, pp. 175-183, 2003
15. Wilcox P., Lowe M., Cawley P., 'The effect of dispersion on long-range inspection using ultrasonic guided waves', NDT&E international 34, pp. 1-9, 2001
16. Lamb H., 'On the propagation of tremors over the surface of an elastic solid', Phil. Trans. R. Soc. A203, pp. 1-42, 1904
17. Miller G. F., Pursey H., 'The field and radiation impedance of mechanical radiators on the free surface of a semi-infinite isotropic solid.', Proc. R. Soc. 223, pp. 521-541, 1954
18. Achenbach J. D., 'Wave propagation in elastic solids', North-Holland Publishing Company, pp. 283-289, 1975

What is claimed is:

1. A method of ultrasonic testing of a solid object, the method comprising:
    attaching a proximal end of an elongate strip having a width and a thickness and a width to thickness aspect ratio of greater than unit to a solid object;
    coupling a transducer to the elongate strip;
    exciting non-dispersive ultrasonic signals in the elongate strip with the transducer, the signals propagating along a length of the elongate strip toward the proximal end and into the solid object, said signals comprising shear wave signals which are polarized in a direction perpendicular to their propagation direction; and
    receiving corresponding reflected return signals from said solid object that are non-dispersive ultrasonic shear wave signals and are polarized in a direction perpendicular to a propagation direction of the reflected return signals.

2. The method of claim 1, wherein said elongate strip is formed of a material having a shear velocity of $C_s$ and a shear wavelength $\lambda_B$, where $\lambda_B = C_s/F$ and F is the frequency corresponding to $\lambda_B$, and said substantially non-dispersive ultrasonic pulses are formed of components of different frequencies and having shear wavelengths extend from $\lambda_{short}$ to $\lambda_{long}$.

3. The method of claim 2 wherein said elongate strip has a transverse cross-section with a thickness less than 2.5 $\lambda_{short}$.

4. The method of claim 2, wherein said elongate strip has a transverse cross-section with a thickness less than $\lambda_{short}$.

5. The method of claim 2, wherein said elongate strip has a transverse cross-section with a width greater than 3.5 $\lambda_{long}$.

6. The method of claim 2, wherein said elongate strip has a transverse cross-section with a width greater than 5 $\lambda_{long}$.

7. The method of claim 1, wherein said elongate strip is formed of a material having a bar velocity $C\lambda_{bar}$, and a wavelength $\lambda_{bar}$, where $\lambda_{bar} = C_{bar}/F$ and F is the frequency corresponding to $\lambda_{bar}$, and said substantially non-dispersive ultrasonic signals are formed of components of different frequencies and having bar wavelengths extending from $\lambda_{short}$ to $\lambda_{long}$.

8. The method of claim 7, wherein said thickness is less than 2.5 $\lambda_{short}$.

9. The method of claim 7, wherein said thickness is less than $\lambda_{short}$.

10. The method of claim 7, wherein said width is greater than 5 $\lambda_{long}$.

11. The method of claim 1, wherein substantially only a single mode of propagated guided wave is excited in said elongate waveguide.

12. The method of claim 1, wherein said object under test is:
    (i) at a temperature great than 200° C.; and
    (ii) subject to the above background levels ionizing radiation.

* * * * *

UNITED STATES PATENT AND TRADEMARK OFFICE
CERTIFICATE OF CORRECTION

| | | |
|---|---|---|
| PATENT NO. | : 9,274,090 B2 | Page 1 of 1 |
| APPLICATION NO. | : 14/291467 | |
| DATED | : March 1, 2016 | |
| INVENTOR(S) | : Peter Cawley et al. | |

It is certified that error appears in the above-identified patent and that said Letters Patent is hereby corrected as shown below:

In the claims,

Column 12, Line 61, Claim 12:

After "(i) at a temperature"
Delete "great" and
Insert -- greater --.

Signed and Sealed this
Twenty-fourth Day of May, 2016

Michelle K. Lee
*Director of the United States Patent and Trademark Office*